United States Patent [19]

Martinez, Jr.

[11] Patent Number: 5,038,499
[45] Date of Patent: Aug. 13, 1991

[54] SEPARABLE SHOE STRAP CONSTRUCTION

[76] Inventor: Ramon Martinez, Jr., 7115 Sunlit Trail, San Antonio, Tex. 78244

[21] Appl. No.: 486,299

[22] Filed: Feb. 28, 1990

[51] Int. Cl.$^5$ .............................................. A43B 23/28
[52] U.S. Cl. ...................................... 36/58.5; 36/136; 36/1
[58] Field of Search ........................ 36/11.5, 90, 1, 88, 36/89, 105, 136, 132, 58.5, 58.6; 128/80 H, 893, 166

[56] References Cited

U.S. PATENT DOCUMENTS

| | | | |
|---|---|---|---|
| 1,109,107 | 9/1914 | Barnes | 36/58.5 |
| 1,422,683 | 7/1922 | Eltgroth | 36/136 |
| 1,598,504 | 8/1926 | Pierce et al. | 128/80 H |
| 2,496,782 | 2/1950 | Engel | 36/11.5 |
| 2,936,533 | 5/1960 | Paynor | 36/105 |
| 3,057,085 | 10/1962 | Rigsby | 36/11.5 |
| 3,197,793 | 8/1965 | Walters | 36/1 |
| 3,314,090 | 4/1967 | Azzarito | 36/1 |
| 4,289,122 | 9/1981 | Mason et al. | 128/80 H |

FOREIGN PATENT DOCUMENTS

| | | | |
|---|---|---|---|
| 309978 | 12/1918 | Fed. Rep. of Germany | 36/89 |
| 708497 | 7/1931 | France | 30/89 |
| 964740 | 8/1950 | France | 30/89 |
| 17220 | of 1907 | United Kingdom | 36/58.5 |
| 172254 | 12/1921 | United Kingdom | 36/58.5 |

OTHER PUBLICATIONS

"Self-Adhering Nylon Tapes", Maurice Gershman, Journal of the A.M.A. 10/1958.

*Primary Examiner*—Steven N. Meyers
*Attorney, Agent, or Firm*—Leon Gilden

[57] ABSTRACT

A shoe strap is arranged for securement to an existing shoe construction wherein the shoe strap includes a flexible surrounding strap for securement about an ankle of an individual with a securement buckle portion mounted cooperatively at forward terminal ends of the surrounding strap. A downwardly extending rigid leg includes a mounting for one of a plurality of fastener members for securement and cooperation with an associated shoe. The fastener members are adhesively or mechanically mounted to the downwardly extending leg and include a flexible pad to be positioned overlying the inner sole of the associated shoe, a clamp member, a tooth engagement.

1 Claim, 4 Drawing Sheets

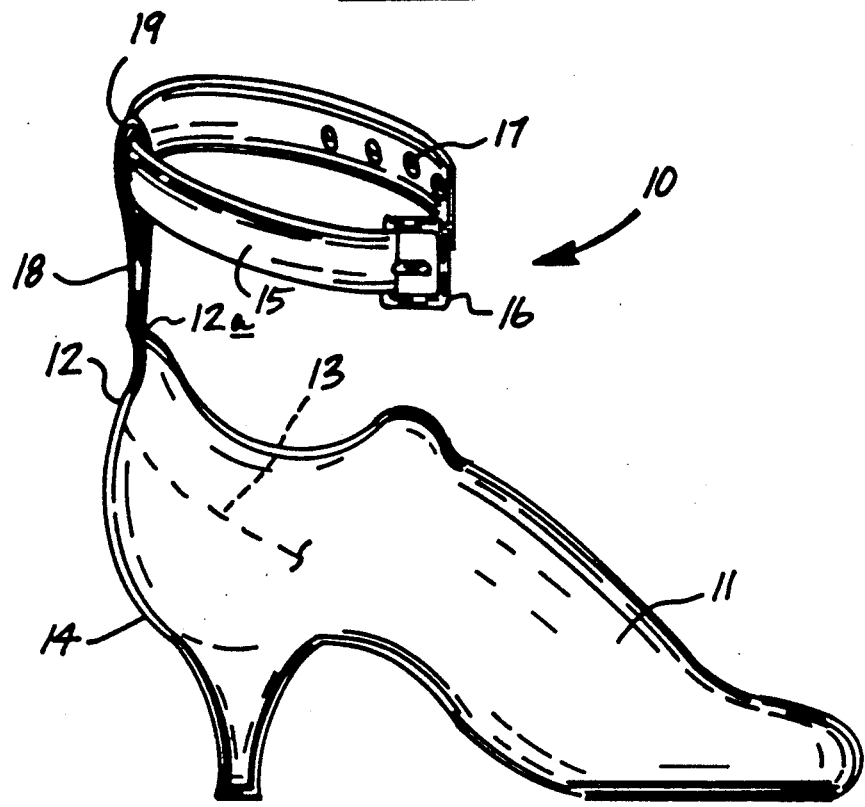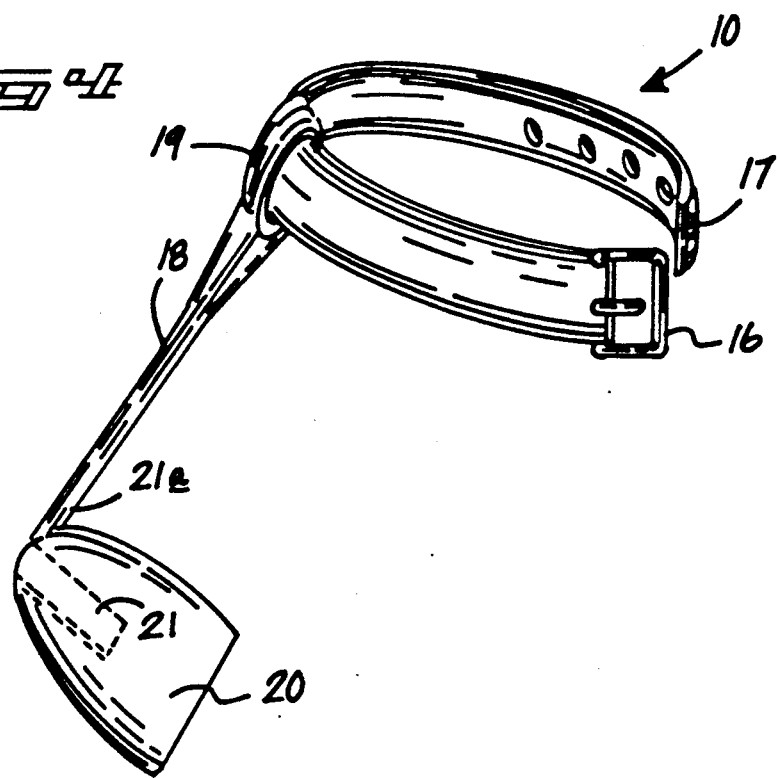

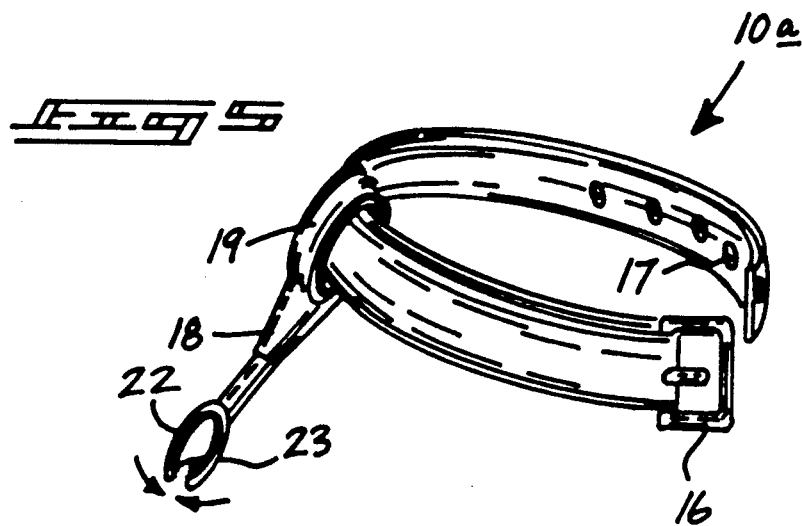
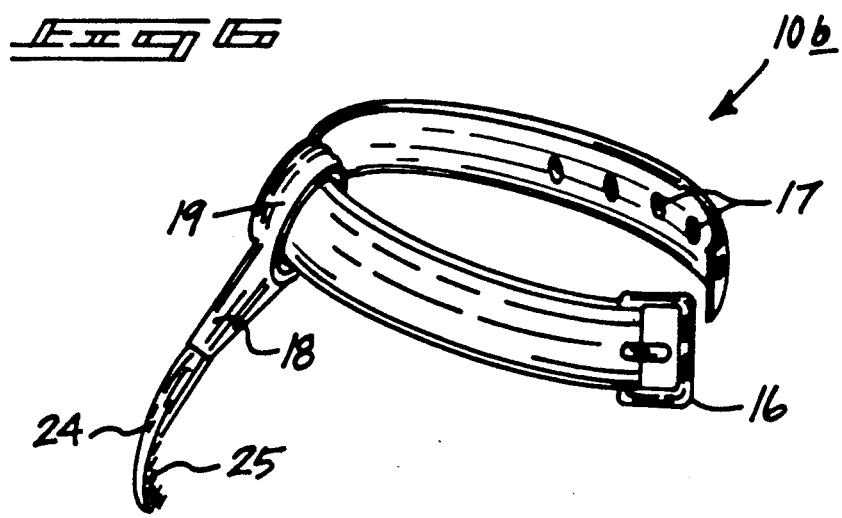

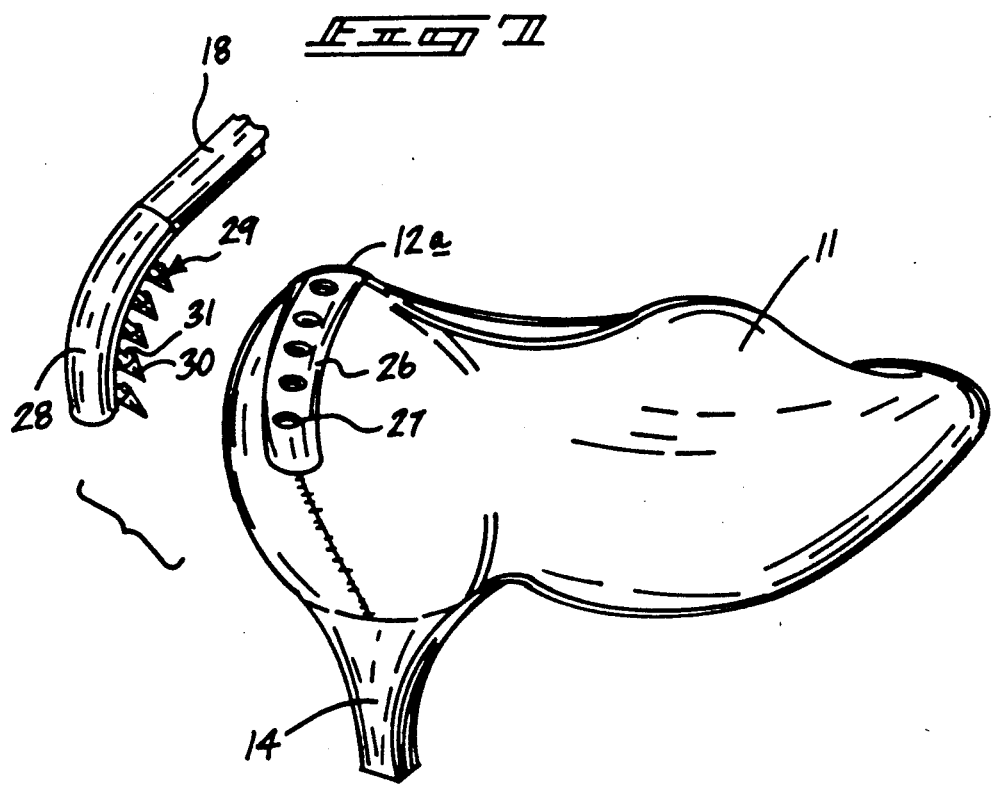
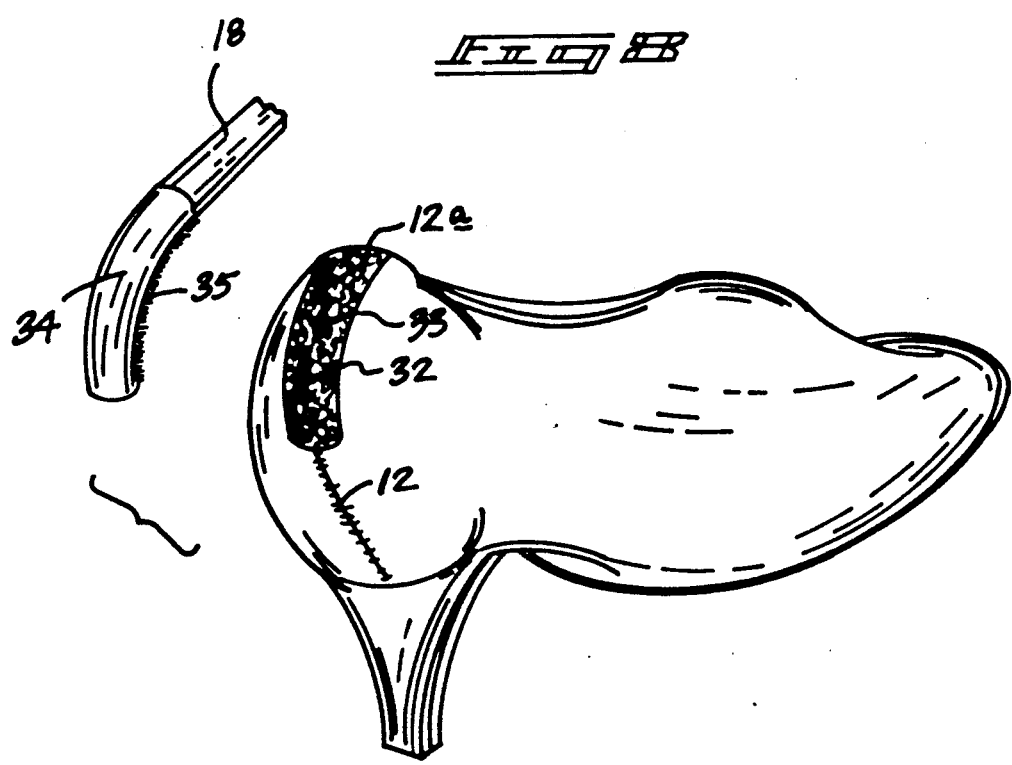

SEPARABLE SHOE STRAP CONSTRUCTION

BACKGROUND OF THE INVENTION

1. Field of the Invention

The field of the invention relates to shoe construction, and more particularly pertains to a new and improved separable shoe strap kit wherein the same permits selective association and mounting of an ankle strap to an existing shoe structure.

2. Description of the Prior Art

Ankle straps have been utilized in cooperation with shoe structures to provide enhanced securement of an associated shoe to an ankle and leg portion of a wearer of the shoe as well as to accommodate contemporary fashion requirements.

Prior art ankle strap arrangements have typically been mounted in fixed manner relative to prior art shoe structures wherein individuals have been required to purchase replacement shoes in order to avail themselves of the use of an ankle strap arrangement. Examples of the prior art include U.S. Pat. No. 2,582,910 to LYON illustrative of an ankle strap arrangement utilizing either a single strap or a laced network to secure an upwardly extending extension of a rear portion of the shoe to an individual's ankle.

U.S. Pat. No. 2,750,684 to LYON illustrates the use of an ankle strap mounted to a insole projecting segment mounted to an existing shoe.

U.S. Pat. No. 4,523,394 to LINDH provides a foot ligament protective device utilizing a surrounding strap mounted to spaced loop members where underlying support surface mounting an individual's foot thereon.

U.S. Pat. No. 4,821,743 to WETZ utilizes insole and ankle extensions mounted to an ankle brace to secure an individual's ankle between the extensions.

U.S. Pat. No. 3,516,180 to THURSTON utilizes a guard for use with a ski boot and the like defined by a forward annular rigid member and an encompassing strap for securement about an ankle portion of the rigid member to provide an anti-chaffing barrier in use of the boot.

As such, it may be appreciated that there continues to be a need for a new and improved separable shoe strap kit as addressed by the instant invention which overcomes the problems of ease of use in retrofitt securement of an ankle strap to an introducing shoe structure and in this respect, the present invention substantially fulfills this need.

SUMMARY OF THE INVENTION

In view of the foregoing disadvantages inherent in the known types of ankle strap arrangements for shoes now present in the prior art, the present invention provides a new and improved separable shoe strap kit wherein the same permits ease of selective securement of an ankle to an existing shoe structure. As such, the general purpose of the present invention, which will be described subsequently in greater detail, is to provide a new and improved separable shoe strap kit which has all the advantages of the prior art shoe strap construction and none of the disadvantages.

The separable shoe strap kit of the instant invention essentially includes a shoe strap is arranged for securement to an existing shoe construction wherein the shoe strap includes a flexible surrounding strap for securement about an ankle of an individual with a securement buckle portion mounted cooperatively at forward terminal ends of the surrounding strap. A downwardly extending rigid leg includes a mounting for one of a plurality of fastener members for securement and cooperation with an associated shoe. The fastener members are adhesively or mechanically mounted to the downwardly extending leg and include a flexible pad to be positioned overlying the inner sole of the associated shoe, a clamp member, a tooth engagement member for engagement with the medial rear seam of the shoe, or alternatively the use of mechanical fasteners such as projections engageable within teeth mounted within the shoe or an array of hook and loop fasteners for securement to a companion hook and loop fasteners strip securable to the shoe.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved separable shoe strap kit which has all the advantages of the prior art shoe strap kits and none of the disadvantages.

It is another object of the present invention to provide a new and improved shoe strap kit which may be easily and efficiently manufactured and marketed.

It is a further object of the present invention to provide a new and improved shoe strap kit which is of a durable and reliable construction.

An even further object of the present invention is to provide a new and improved shoe strap kit which is susceptible of a low cost of manufacture with regard to both materials and labor, and which accordingly is then susceptible of low prices of sale to the consuming public, thereby making such shoe strap kits economically available to the buying public.

Still yet another object of the present invention is to provide a new and improved shoe strap kit which provides in the apparatuses and methods of the prior art some of the advantages thereof, while simultaneously overcoming some of the disadvantages normally associated therewith.

Still another object of the present invention is to provide a new and improved shoe strap kit which may be compactly stored when not being utilized.

Yet another object of the present invention is to provide a new and improved separable shoe strap kit wherein the same permits convenience of retrofitt of a shoe strap assemblage onto an existing shoe structure.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an isometric illustration of the instant invention in association with a conventional shoe.

FIG. 4 is an isometric illustration of the invention in association with a securement pad.

FIG. 5 is an isometric illustration of the instant invention in association with a spring clamp.

FIG. 6 is an isometric illustration of the instant invention in association with a tooth engaging strap.

FIG. 7 is an isometric illustration of the instant invention utilizing a securement strap including projecting legs in association with an existing shoe.

FIG. 8 is an isometric illustration of the instant invention utilizing a hook and loop fastener strap mounted to an existing shoe in association with a hook and loop fastener strap in association with a ankle strap of the instant invention.

DESCRIPTION OF THE PREFERRED EMBODIMENT

Figure 1:
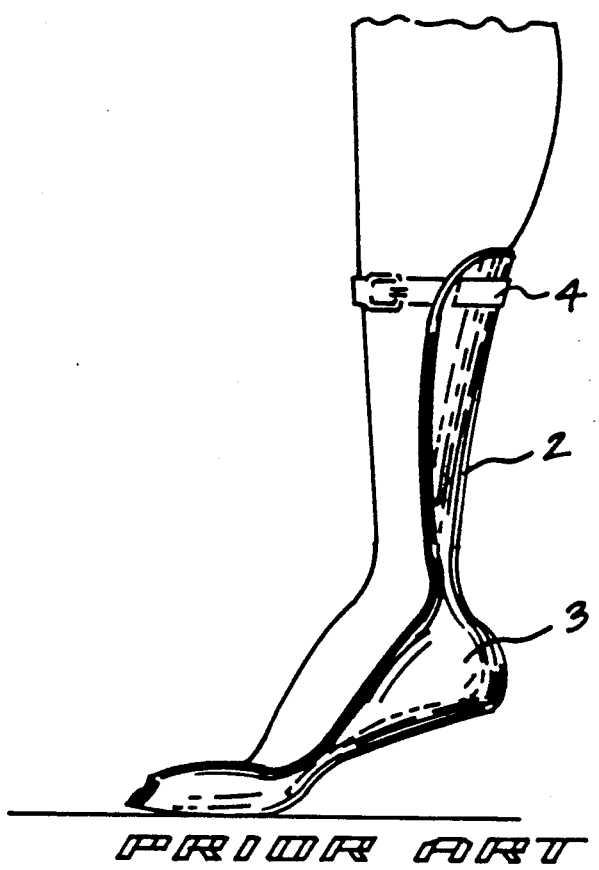
FIG. 1 is an orthographic side view taken in elevation of a prior art ankle shoe strap.

With reference now to the drawings, and in particular to FIGS. 1 to 8 thereof, a new and improved separable shoe strap kit embodying the principles and concepts of the present invention and generally designated by the reference numerals 10, 10a, and 10b will be described.

Figure 2:
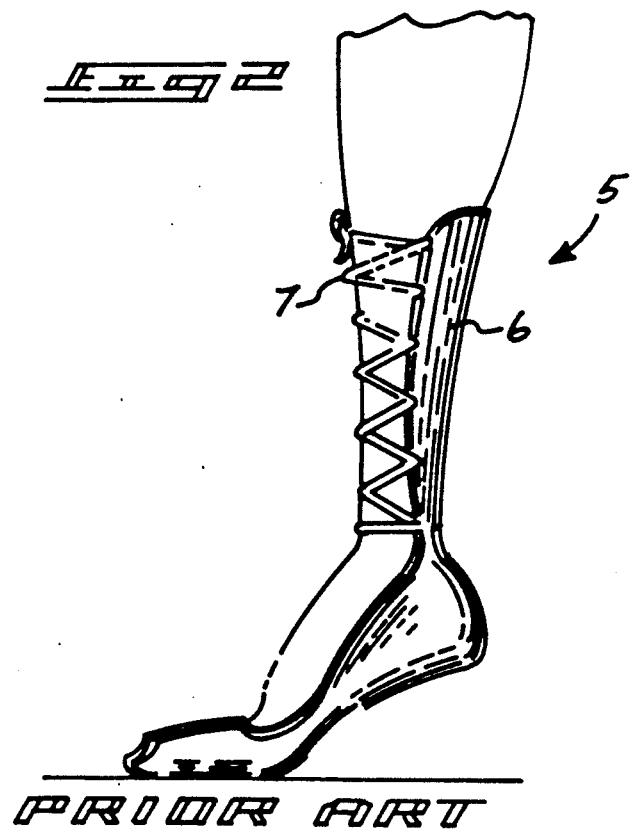
FIG. 2 is an orthographic side view taken in elevation of a further example of a prior art ankle shoe strap.

FIG. 1 illustrates a prior art ankle strap construction 1 wherein a shoe 3 includes an upwardly projecting heel portion 2 with a flexible strap 4 mounted about the upwardly projecting heel portion. FIG. 2 illustrates an analogous construction wherein the projection 6 includes a series of laces 7 to secure the projection to the ankle portion of an individual in the prior art ankle strap construction 5.

More specifically, the separable shoe strap construction kit of the instant invention essentially comprises selective association with a shoe 11 that includes a rear medial seam 12 overlying a heel portion 14. The kit 10 includes a flexible strap 15 including spaced terminal ends wherein a buckle end 16 is operatively associated with an aperture in securement end 17. It is understood of course that selective fashions may be utilized in lieu of the buckle arrangement 16 to secure the free ends of the flexible strap 15 together about an individual's ankle. The strap 15 is slidably mounted through a loop 19 formed at an upper end of a rigid securement leg 18. The rigid securement leg 18 is operably and selectively associated at its lower-most end with a plurality of fasteners to associate the ankle strap 15 with an associated shoe 11.

FIG. 4 illustrates the ankle strap 15 and associated securement leg 18 wherein the fastener comprises a flexible pad 20. A projecting leg 21 is fixedly mounted to the pad 20 interiorly thereof and includes a stub 21a for mechanical or use of securement relative to the securement leg 18 at a lower-most terminal end thereof.

FIG. 5 illustrates the use of a spring mounted C-shaped clip 22 fixedly mounted to a lower-most terminal end of the securement leg 18 wherein the clip 22 includes a plurality of arcuate legs with engaging teeth 23 mounted on lower terminal ends of the legs for securement to an upper edge 12a of the seam 12. FIG. 6 illustrates a further association 10b within the kit wherein a J-shaped lower leg 24 includes an aligned series of engaging teeth 25 mounted to an interior surface of the J-shaped lower leg for inter-engagement with the seam 12 to engage and penetrate the seam for locking association with the seam wherein the J-shaped leg 24 is either adhesively or mechanically mounted to the lower terminal end of the securement leg 18 as illustrated.

FIG. 7 illustrates the use of the securement leg 18 with flexible arcuate locking leg 28 including a series of aligned projections mounted thereon. The projections include an enlarged head portion 30 of a generally conical configuration coaxially aligned with a shank 31 that is in turn integrally mounted in an orthogonal relationship relative to the flexible locking leg 28. The projections 29 are receivable within an aligned series of apertures 27 spaced apart a spacing substantially equal to the spacing between the projections 29. The apertures 27 are mounted within an aperture strap 26 secured to the seam 12 of the shoe in alignment therewith and extending upwardly to the upper edge 12a. Alternatively a second strap 34 mounted to the lower terminal end of the securement leg 18 is of flexible construction and utilizes a second hook and loop fastener surface 35 selectively and operatively associated with a first hook and loop fastener surface 33 of a first strap 32 that is mounted in aligned relationship to the seam 12 and extends medially of the seam upwardly to the upper edge 12a of the seam and associated shoe.

Accordingly the kit provides a series of various fastener members that are securable to the securement leg 18 to permit association with an existing shoe structure 11. Accordingly the manner of usage and operation of the instant invention, the same should be apparent from the above disclosure and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A separable shoe strap kit in combination with a shoe structure for selective securement to the shoe structure, the shoe structure including:

an upper, a sole, a heel portion of the upper having an elongate seam directed from the heel portion of the sole upwardly to an upper seam edge, the kit including a flexible strap including a first and second free end, the first end including a first securement member and the second free end including a second securement member wherein the first and second securement members are selectively securable together to encompass an ankle portion of an individual, the kit further including a rigid securement leg directed downwardly from the strap wherein the securement leg includes a loop formed to an upper terminal end thereof, the flexible strap slidably receivable within the loop, and a fastening means attached to a lower terminal end of the securement leg for securement to the shoe, wherein the fastening means includes a flexible locking leg, the flexible locking leg including an aligned series of projections spaced apart by a predetermined spacing, each projection including an enlarged conical head portion coaxially aligned with a shank, each shank fixedly mounted to an interior surface of the flexible locking leg, and an apertured strap mounted overlying the seam medially thereof and projecting upwardly to the seam edge and the apertured strap including a series of aligned apertures spaced apart by a predetermined spacing for reception of the projections therewithin.

* * * * *